United States Patent [19]

Stables

[11] 4,298,732
[45] Nov. 3, 1981

[54] CRYSTALLIZATION PROCESS

[75] Inventor: Harry C. Stables, Ulverston, England

[73] Assignee: Glaxo Group Limited, England

[21] Appl. No.: 126,523

[22] Filed: Mar. 3, 1980

Related U.S. Application Data

[63] Continuation of Ser. No. 4,071, Jan. 17, 1978, abandoned.

[30] Foreign Application Priority Data

Jan. 17, 1978 [GB] United Kingdom ................. 1881/78

[51] Int. Cl.³ ............................................ C07D 501/12
[52] U.S. Cl. ......................................... 544/20; 544/22
[58] Field of Search ..................................... 544/20, 22

[56] References Cited

U.S. PATENT DOCUMENTS 3,714,154  1/1973  Pfeiffer et al. ....................... 544/20
3,974,153  8/1976  Cook et al. ........................... 544/22

OTHER PUBLICATIONS

Murthy et al., "Organic Chemistry Made Simple", (1962), p. 258.
Ault, "Techniques and Experiments for Organic Chemistry", (1976), pp. 53 & 90.

Primary Examiner—Paul M. Coughlan, Jr.
Attorney, Agent, or Firm—Bacon & Thomas

[57] ABSTRACT

A process for the preparation of crystalline sodium cefuroxime (the sodium salt of (6R,7R)-3-carbamoyloxymethyl-7-[(Z)-2-(fur-2-yl)-2-methoxyiminoacetamido]ceph-3-em-4-carboxylic acid) which comprises adding an aqueous solution of sodium cefuroxime and an aqueous solution containing sodium ions to an aqueous crystallizing medium containing a seeding amount of solid sodium cefuroxime and recovering crystalline sodium cefuroxime from the crystalline medium. The process enables the production of crystalline sodium cefuroxime on an industrial scale in a condition of sufficient sterility, purity and solid state stability for use in pharmaceutical preparations.

11 Claims, No Drawings

CRYSTALLIZATION PROCESS

This is a continuation of application Ser. No. 004,071, filed Jan. 17, 1978, now abandoned.

The present invention is concerned with improvements in or relating to the production of the sodium salt of (6R,7R)-3-carbamoyloxymethyl-7-[(Z)-2-(fur-2-yl)-2-methoxyimino-acetamido]ceph-3-em-4-carboxylic acid (hereinafter referred to as cefuroxime) in crystalline form.

Cefuroxime, as disclosed in British Patent Specification No. 1,453,049 is a valuable, broad-spectrum antibiotic characterised by high activity against a wide range of gram-positive and gram-negative microorganisms, this property being enhanced by the very high stability of the compound to $\beta$-lactamases produced by a range of gram-negative microorganisms. Additionally, the compound is stable in the body owing to its resistance to the action of mammalian esterases, and gives high serum levels following parenteral administration (e.g. in the form of the sodium salt) to human and animal subjects, while exhibiting low serum binding.

The sodium salt of cefuroxime (hereinafter referred to as sodium cefuroxime) is of particular importance since it enables cefuroxime to be formulated in aqueous pharmaceutical compositions for injection. There is thus a need to produce sodium cefuroxime in as pure and homogeneous a condition as possible in order to fulfil exacting pharmaceutical requirements and specifications. The sodium cefuroxime should be produced in the final stage in a sterile form and this is advantageously achieved by conducting the operating processes of crystallisation, recovery and drying under sterile conditions, preferably in a closed system.

Sodium cefuroxime exists in a number of different crystalline forms of varying degrees of solid state stability and purity and with differing physical and chemical characteristics.

It has proved difficult in practice to manufacture sterile sodium cefuroxime industrially in a crystalline form having a combination of suitable properties such as solid state stability, purity, particle size, filtration and drying characteristics.

The process of the present invention enables crystalline sodium cefuroxime to be readily recovered in a sterile form from a solution containing it, on an industrial scale, in a condition of sufficient purity and solid state stability for use in pharmaceutical preparations. This crystalline material has been found to have particularly good filtration and drying characteristics.

According to the present invention there is provided a process for the preparation of crystalline sodium cefuroxime which comprises adding an aqueous solution of sodium cefuroxime and an aqueous solution containing sodium ions to an aqueous crystallising medium containing a seeding amount of solid sodium cefuroxime and recovering crystalline sodium cefuroxime from the crystallising medium, wherein the crystallising medium is at a temperature of from 20° to 60° C. and the aqueous solution of sodium cefuroxime and the aqueous solution containing sodium ions are added substantially simultaneously and at substantially the same volume rate whereby sodium cefuroxime continuously crystallises out of the crystallising medium as the two solutions are added.

The sodium ions in the aqueous solution which is added to the crystallising medium may be derived from a variety of non-toxic, water-soluble sodium salts. It is, however, generally preferred to employ a sodium salt which is not only soluble in water but which is also soluble in lower alcohols or ketones e.g. methanol, ethanol and acetone. Particularly preferred sodium salts are those derived from organic carboxylic acids, for example, acetic, 2-ethylhexanoic, lactic, gluconic, glutaric, maleic, fumaric and citric acid. Sodium lactate and sodium acetate are especially preferred.

The above-mentioned sodium salts may be employed in the aqueous solution for example in concentrations of 20 to 70%, preferably 30 to 50% w/v.

The aqueous solution of sodium cefuroxime which is added to the crystallising medium may have a concentration of 5 to 20%, preferably 10 to 20% w/v.

The aqueous crystallising medium containing the sodium cefuroxime seed advantageously contains sodium ions, other than those derived from the solid sodium cefuroxime, for example, derived from non-toxic, water-soluble sodium salts such as those described above.

The initial crystallising medium preferably contains solid sodium cefuroxime in an amount sufficient to maintain a mobile slurry and to initiate a constant crystallisation sequence on addition of the streams of sodium cefuroxime and the other sodium salt thereto. Where the initial crystallising medium contains both sodium cefuroxime and another sodium salt, the latter should desirably be present in such an amount as to prevent the solid sodium cefuroxime going into solution.

The aqueous solutions containing the sodium ions, the sodium cefuroxime and the aqueous crystallising medium may if desired be diluted with a co-solvent e.g. a polar organic solvent such as a lower alkanol, for example methanol or ethanol, or a lower alkyl ketone, for example acetone.

In order to ensure that the sodium cefuroxime crystallises out of the crystallising medium in a satisfactory fashion, the crystallising medium is maintained at a temperature of from 20° to 60° C., advantageously from 40° to 50° C. The sodium cefuroxime solution to be added is preferably at a temperature of, for example 10° to 35° C., advantageously 15° to 25° C. The temperature of the aqueous solution containing the sodium ions to be added is relatively unimportant but a temperature of for example 10° to 50° C. is generally convenient.

The sodium cefuroxime solution is advantageously treated with charcoal and filtered prior to addition to the crystallising medium.

The sodium cefuroxime solution and the aqueous solution containing sodium ions are preferably added to the crystallising medium over a period of 1 to 5 hours, particularly 2 to 3 hours. The sodium cefuroxime solution and the aqueous solution containing sodium ions are preferably added to the crystallising medium in such a way that the sodium cefuroxime crystallises out in the crystallising medium at a similar rate to that at which it is added.

As the addition of the two solutions proceeds, the crystallising medium is desirably kept in a state of agitation to facilitate the crystallisation of the sodium cefuroxime. This can be filtered off, if desired after cooling, washed and dried.

The solid sodium cefuroxime used in the crystalline medium in accordance with the invention is preferably Form II crystalline sodium cefuroxime as described in the above-mentioned British Patent Specification No. 1,453,049. The use of such crystalline Form II in the process according to the present invention leads to the production of crystalline sodium cefuroxime which is basically Form II, but having improved crystallographic characteristics. A particular advantage of this improved crystalline form of sodium cefuroxime is its increased solid state stability.

The following Examples illustrate the present invention. The charcoal employed was the Norit Ultra brand.

EXAMPLE 1

Sodium cefuroxime (10 g) is dissolved in water (60 ml) at 25°–30° C. Charcoal (1 g) is added, the mixture stirred for 30 mins., filtered and the charcoal washed with water (10 ml). The bulked filtrates are then added at 20° to a stirred slurry of sodium cefuroxime (Form II; 0.1 g) in 25% w/v sodium lactate aqueous solution (20 ml) maintained at 50° C. over 3 hours. Simultaneously, an aqueous solution of 50% w/v sodium lactate (70 ml) at 20° C. is added over the same period of time.

The mixture is then cooled to 5° C., filtered, and the product washed with industrial methylated spirits (100 ml) and dried in vacuo. The product had $[\alpha]_D^{20} + 63.5°$ (c 0.5, pH 4.5 phosphate buffer) and $\lambda$ max 273 nm; $E_1{}_{cm}^{1\%}$ 396 ($H_2O$).

EXAMPLE 2

Sodium cefuroxime (15 g) is dissolved in water (90 ml) at 25°–30° C. Charcoal (1.5 g) is added, the mixture stirred for 30 mins., filtered and the charcoal washed with water (10 ml). The bulked solution, at ambient temperature, is added to a slurry of sodium cefuroxime (Form II; 0.15 g) in an aqueous solution of 20% w/v sodium acetate (20 ml) at 50° C. over 3 hours. Simultaneously, an aqueous solution of 40% w/v sodium acetate (100 ml) at 50° C. is added over the same period of time. The mixture is then cooled to 5° C., filtered and the product washed with industrial methylated spirits (150 ml) and dried in vacuo; $E_1{}_{cm}^{1\%}$ (273 nm) 400 and $[\alpha]_D^{20} + 62.5°$ (c 0.5, pH 4.5 phosphate buffer).

EXAMPLE 3

Sodium cefuroxime (10 g) is dissolved in water (70 ml) at 25°–30° C. Charcoal (1 g) is added, the mixture stirred for 30 mins., filtered and the charcoal washed with water (10 ml). The bulked filtrates, at ambient temperature, are added to a slurry of sodium cefuroxime (Form II; 0.1 g) in 25% w/v aqueous sodium lactate (20 ml) maintained at 50° C. over 2 hours. Simultaneously an aqueous solution of 50% w/v sodium lactate (80 ml) mixed with industrial methylated spirits (30 ml) is added over the same period of time. The mixture is then cooled to 0° C., filtered and the product washed with industrial methylated spirits (100 ml) then dried in vacuo; $E_1{}_{cm}^{1\%}$ (273 nm) 407 and $[\alpha]_D^{20} + 61.1°$ (c 0.5, pH 4.5 phosphate buffer).

I claim:

1. In a process for the preparation of crystalline sodium cefuroxime wherein the improvement comprises the steps of adding an aqueous solution containing from 5 to 20% w/v of sodium cefuroxime and an aqueous solution containing sodium ions derived from a non-toxic, water-soluble sodium salt of an organic carboxylic acid other than those derived from sodium cefuroxime, and having a concentration of from 20 to 70% w/v; to an aqueous crystallising medium containing a seeding amount of solid sodium cefuroxime and recovering crystalline sodium cefuroxime from the crystallising medium, the crystallising medium being at a temperature of from 20° to 60° C. and the aqueous solution of sodium cefuroxime and the aqueous solution containing sodium ions being added substantially simultaneously and at substantially the same volume rate, whereby sodium cefuroxime continuously crystallises out of the crystallising medium as the two solutions are added.

2. A process as claimed in claim 1 wherein in the aqueous solution containing sodium ions, the sodium ions are derived from a compound selected from the group consisting of sodium lactate and sodium acetate.

3. A process as claimed in claim 1 wherein the crystallising medium contains sodium ions other than those derived from the solid sodium cefuroxime, in an amount sufficient to prevent the solid sodium cefuroxime from going into solution, which sodium ions are derived from a non-toxic, water-soluble sodium salt.

4. A process as claimed in claim 1 wherein the aqueous solution of sodium cefuroxime to be added is at a temperature of from 10° to 35° C.

5. A process as claimed in claim 1 wherein the sodium cefuroxime solution and the solution containing sodium ions are added to the crystallising medium over a period of 2 to 3 hours.

6. A process as claimed in claim 1 wherein the crystallising medium is at a temperature of from 40° to 50° C.

7. The process as defined in claim 1 wherein the carboxylic acid is selected from the group consisting of acetic, 2-ethylhexanoic, lactic, gluconic, glutaric, maleic, fumaric and citric acid.

8. The process as defined in claim 1 wherein the amount of sodium salt in the sodium ions containing solution is from 30 to 50% and the amount of sodium cefuroxime in the sodium cefuroxime solution is from 10 to 20% w/v.

9. The process as defined in claim 1 wherein the sodium ions containing solution has a temperature of from 10° to 50° C., and the sodium cefuroxime solution is at a temperature of from 10° to 35° C.

10. The process as defined in claim 9 wherein the temperature of the sodium cefuroxime solution is from 15° to 25° C. and the temperature of the crystallising medium is from 40° to 50° C.

11. The process as defined in claim 1 wherein the water soluble sodium salt is sodium acetate or sodium lactate and the crystallising medium is a slurry comprising an initial seeding amount of from 0.5 to 0.75% w/v of solid sodium cefuroxime in an aqueous solution of from 20 to 25% w/v of the water soluble sodium salt.

* * * * *